US010501315B2

(12) United States Patent
Farrow et al.

(10) Patent No.: US 10,501,315 B2
(45) Date of Patent: Dec. 10, 2019

(54) ANALYTICAL NANOSCOPE ON A CHIP FOR SUB-OPTICAL RESOLUTION IMAGING

(71) Applicant: New Jersey Institute of Technology, Newark, NJ (US)

(72) Inventors: Reginald C. Farrow, Somerset, NJ (US); Alokik Kanwal, Princeton, NJ (US); Arooj A. Aslam, Paterson, NJ (US)

(73) Assignee: New Jersey Institute of Technology, Newark, NJ (US)

(*) Notice: Subject to any disclaimer, the term of this patent is extended or adjusted under 35 U.S.C. 154(b) by 379 days.

(21) Appl. No.: 15/601,357

(22) Filed: May 22, 2017

(65) Prior Publication Data

US 2017/0334717 A1    Nov. 23, 2017

Related U.S. Application Data

(60) Provisional application No. 62/340,195, filed on May 23, 2016.

(51) Int. Cl.
| | |
|---|---|
| *B82B 1/00* | (2006.01) |
| *B82B 3/00* | (2006.01) |
| *G01N 27/12* | (2006.01) |
| *G01N 27/27* | (2006.01) |
| *G01N 27/414* | (2006.01) |

(Continued)

(52) U.S. Cl.
CPC .......... *B82B 1/001* (2013.01); *B82B 3/0014* (2013.01); *G01N 27/127* (2013.01); *G01N 27/27* (2013.01); *G01N 27/4146* (2013.01); *B82Y 10/00* (2013.01); *B82Y 15/00* (2013.01);
(Continued)

(58) Field of Classification Search
None
See application file for complete search history.

(56) References Cited

U.S. PATENT DOCUMENTS

| | | |
|---|---|---|
| 7,736,979 B2 | 6/2010 | Farrow et al. |
| 7,964,143 B2 | 6/2011 | Farrow et al. |

(Continued)

OTHER PUBLICATIONS

Arnold, et al., "Hydrodynamic Characterization of Surfactant Encapsulated Carbon Nanotubes Using an Analytical Ultracentrifuge", ACS Nano, vol. 2, No. 11, Oct. 2008, pp. 2291-2300.

(Continued)

*Primary Examiner* — Hoon K Song
(74) *Attorney, Agent, or Firm* — Lerner, David, Littenberg, Krumholz & Mentlik, LLP

(57) ABSTRACT

An imaging device and method of using is provided that requires no traditional optics but uses an addressable array of vertically oriented carbon nanotubes. The technique relies on the ability to reduce the nearest neighbor spacing between the carbon nanotubes to less than the wavelength of light used in traditional optical microscopes. The nanoscope can have a resolution of less than 100 nm. Electrophoresis deposition can be used to direct the assembly of the carbon nanotubes onto interconnects in an integrated circuit, which could be used to address the array. The device is portable, compact, and does not utilize complicated components. It also derives spatially resolved dielectric and chemical properties of a sample to be imaged.

11 Claims, 5 Drawing Sheets

(51) Int. Cl.

| | |
|---|---|
| H01L 51/00 | (2006.01) |
| B82Y 10/00 | (2011.01) |
| B82Y 15/00 | (2011.01) |
| G01N 27/22 | (2006.01) |
| G01N 27/327 | (2006.01) |
| G01N 33/487 | (2006.01) |

(52) U.S. Cl.
CPC ....... *G01N 27/227* (2013.01); *G01N 27/3278* (2013.01); *G01N 33/48728* (2013.01); *H01L 51/0048* (2013.01)

(56) References Cited

U.S. PATENT DOCUMENTS

| | | |
|---|---|---|
| 8,257,566 B2 | 9/2012 | Farrow et al. |
| 8,546,027 B2 | 10/2013 | Farrow et al. |
| 2013/0341185 A1* | 12/2013 | Collaert ................ B82Y 30/00 204/403.01 |

OTHER PUBLICATIONS

Bai, et al., "Carbon Nanotube Schottky Diode: An Atomic Perspective", Nanotechnology, vol. 19, No. 11, Feb. 2008, 7 pages.
Calderon-Colon, et al., "A Carbon Nanotube Field Emission Cathode with High Current Density and Long-Term Stability", Nanotechnology, vol. 20, No. 32, Jul. 2009, 6 pages.
Chen, et al., "The Role of Metal-Nanotube Contact in the Performance of Carbon Nanotube Field-Effect Transistors", Nano Letters, vol. 5, No. 7, Jul. 2005, pp. 1497-1502.
Choi, et al., "Electrophoresis Deposition of Carbon Nanotubes for Triode-Type Field Emission Display", Applied Physics Letters, vol. 78, No. 11, Mar. 2001, pp. 1547-1549.
Delgado et al., "Measurement and Interpretation of Electrokinetic Phenomena", Journal of Colloid and Interface Science, vol. 309, No. 2, May 2007, pp. 194-224.
Fagan, et al., "Length Fractionation of Carbon Nanotubes Using Centrifugation", Advanced Materials, vol. 20, No. 9, May 2008, pp. 1609-1613.
Franklin, et al., "Vertical Carbon Nanotube Devices with Nanoscale Lengths Controlled Without Lithography", IEEE Transactions on Nanotechnology, vol. 8, No. 4, Jul. 2009, pp. 469-476.
Gao, et al., "Fabrication and Electron Field Emission Properties of Carbon Nanotube Films by Electrophoretic Deposition", Advanced Materials, vol. 13, No. 23, Dec. 2001, pp. 1770-1773.
Goyal, et al., "Directed Self-Assembly of Individual Vertically Aligned Carbon Nanotubes", Journal of Vacuum Science & Technology B: Microelectronics and Nanometer Structures Processing, Measurement, and Phenomena, vol. 26, No. 6, Nov. 2008, pp. 2524-2528.
Graham, et al., "How Do Carbon Nanotubes Fit into the Semiconductor Roadmap?", Applied Physics A, vol. 80, No. 6, Mar. 2005, pp. 1141-1151.
Jeong, et al., "Highly Stretchable Reduced Graphene Oxide (rGO)/Single-walled Carbon Nanotubes (SWNTs) Electrodes for Energy Storage Devices", Electrochimica Acta, vol. 163, May 2015, pp. 149-160.
Kanwal, et al., "Scalable Nano-Bioprobes with Sub-Cellular Resolution for Cell Detection", Biosensors and Bioelectronics, vol. 45, Jul. 2013, pp. 267-273.
Kanwal, et al., "Substantial Power Density From a Discrete Nano-Scalable Biofuel Cell", Electrochemistry Communications, vol. 39, Feb. 2014, pp. 37-40.
Kinaret, et al., "A Carbon-Nanotube-based Nanorelay", Applied Physics Letters, vol. 82, No. 8, Feb. 2003, pp. 1287-1289.
Krompiewski, S., "Electronic Transport Through Side-Contacted Graphene Nanoribbons: Effects of Overlap, Aspect Ratio and Orientation", Nanotechnology, vol. 22, No. 44, Oct. 2011, 7 pages.
Lu, et al., "Ultrasensitive Electrochemical Immunosensor Based on Au Nanoparticles Dotted Carbon Nanotube-Graphene Composite and Functionalized Mesoporous Materials", Biosensors and Bioelectronics, vol. 33, No. 1, Mar. 2012, pp. 29-35.
Park, et al., "A Review of Fabrication and Applications of Carbon Nanotube Film-Based Flexible Electronics", Nanoscale, vol. 5, No. 5, 2013, pp. 1727-1752.
Sun, et al., "A Review of Carbon Nanotube- and Graphene-Based Flexible Thin-Film Transistors", Small, vol. 9, No. 8, Apr. 2013, pp. 1188-1205.
Tessonnier, et al., "Recent Progress on the Growth Mechanism of Carbon Nanotubes: A Review", ChemSusChem, vol. 4, No. 7, Jul. 2011, pp. 824-847.
Tulevski, et al., "Toward High-Performance Digital Logic Technology with Carbon Nanotubes", ACS Nano, vol. 8, No. 9, Sep. 2014, pp. 8730-8745.
Volder, et al., "Carbon Nanotubes: Present and Future Commercial Applications", Science, vol. 339, No. 6119, Feb. 2013, pp. 535-539.
Yakobson, et al., "Nanomechanics of Carbon Tubes: Instabilities Beyond Linear Response", Physical Review Letters, vol. 76, No. 14, Apr. 1996, 4 pages.
Yoon, et al., "Intracellular Neural Recording with Pure Carbon Nanotube Probes", PloS One, vol. 8, No. 6, Jun. 2013, 6 pages.
Cui, et al., "Lenslessl-ligh-resolution On-chip Optofluidic Microscopes for Caenorhabditis Elegans and Cell Imaging", PNAS, Aug. 5, 2008, vol. 105, No. 31, pp. 10670-10675.
Zhang, et al., "A Cost-effective Fluorescence Mini-microscope for Biomedical Applications", Lab Chip, Sep. 21, 2015, vol. 15, No. 18, pp. 3661-3669.

* cited by examiner

ANALYTICAL NANOSCOPE ON A CHIP FOR SUB-OPTICAL RESOLUTION IMAGING

CROSS-REFERENCE TO RELATED APPLICATION

The present application claims the benefit of the filing date of U.S. Provisional Patent Application No. 62/340,195, filed May 23, 2016, the disclosure of which is hereby incorporated herein by reference.

FIELD OF THE DISCLOSURE

The present disclosure relates to an imaging device. More particularly, the present disclosure is directed to an analytical nanoscope on a chip for sub-optical resolution imaging.

BACKGROUND

A traditional optical microscope uses a combination of lenses to project light onto a sample and magnify the resulting image. The resolution is a linear function of the wavelength of light. A large numerical aperture is needed for very high resolution, which limits both the field of view and the depth of focus.

Two integrated circuit imaging devices are generally used in cameras for microscopy. These devices serve as cameras on a chip, and are the charged coupled device (CCD) and the complementary metal oxide semiconductor (CMOS) imaging device. These devices primarily convert light into an electrical signal and are coupled with lenses. There are many drawbacks to traditional microscopes. Typically compact traditional optical microscopes have poor resolution. Also current devices require too complicated equipment, take up a lot of space with a large footprint, or are not portable.

There still remains a need in the art for a compact microscope with resolution better than an optical microscope that does not require complicated equipment and has a small footprint and is portable.

SUMMARY

The present invention solves the problems of current state of the art and provides many more benefits. In accordance with embodiments of the present disclosure, an exemplary imaging device is provided that requires no traditional optics but uses an addressable array of vertically oriented carbon nanotubes. The carbon nanotubes may be functionalized to provide chemical information about a sample. The technique relies on the ability to reduce the nearest neighbor spacing between the carbon nanotubes to less than the wavelength of light used in traditional optical microscopes. The nanoscope can have a resolution of less than 100 nm in one embodiment. Electrophoresis deposition can be used to direct the assembly of the carbon nanotubes onto interconnects in an integrated circuit, which could be used to address the array. In another embodiment, methods are described to derive spatially resolved dielectric and chemical properties of the sample to be imaged.

Unlike other devices, the nanoscope of the present invention does not need light and can collect information directly from the sample by making contact or converting the information from a functional molecule. Furthermore, unlike versions requiring a "flowing" fluid medium to achieve sub-pixel resolution, the present invention achieves better resolution than the flowing medium version without requiring flow of any medium.

The device and method relies on the ability to reduce the nearest neighbor spacing between the carbon nanotubes to less than the wavelength of light used in traditional optical microscopes. Again, the nanoscope can have resolution of less than 100 nm, and electrophoresis deposition can be used to direct the assembly of the carbon nanotubes onto interconnects in an integrated circuit that may be used to address the array. Apparatus and methods of the present invention derive spatially resolved dielectric and chemical properties of the sample to be imaged.

Any combination and/or permutation of the embodiments are envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

To assist those of skill in the art in making and using the disclosed imaging device and associated systems and methods, reference is made to the accompanying figures, wherein.

DETAILED DESCRIPTION

Exemplary embodiments are directed to imaging devices. Although discussed herein with respect to an analytical nanoscope, it should be understood that embodiments can generally be applied to other imaging devices.

It was found that an array of appropriate sensors in close proximity to a material can derive the spatial variation of the properties of that material by sampling the dielectric and/or chemical nature of the material directly. One useful embodiment of this concept is to image the structure and properties of biological samples such as cells in a liquid suspension that is in physical contact or close proximity with the array of sensors.

An array of vertically oriented carbon nanotubes that are wired in such a way that each can be addressed individually forms the basis for the present imaging device. This first requirement is the most challenging since it requires a method to either grow or deposit the carbon nanotubes in a way that allows integration with multiplexing electronics. Because the tips of the carbon nanotubes are exposed and act as sensors, their deposition is integrated into the metal level process of the circuit (i.e., backend process). The traditional methods for growth involve chemical vapor deposition, which generally requires elevated temperatures that are not compatible with backend processing of complementary metal oxide semiconductor (CMOS) integrated circuits. Elevated temperatures at this stage may change the dopant profiles of the transistors or cause diffusion of materials in an unacceptable fashion. An embodiment of the current invention provides a method to fabricate the sensor array of the microscope using electrophoresis deposition of presorted carbon nanotubes, which is a room temperature process.

Depending on the embodiment, the imaging device can be fabricated by incorporating the vertical carbon nanotube sensors into a CMOS addressing architecture. While the use of CMOS is exemplary, it will be understood that other integrated circuits or sensors could be employed, such as a charge-couple device (CCD) image sensor.

Figure 1A:
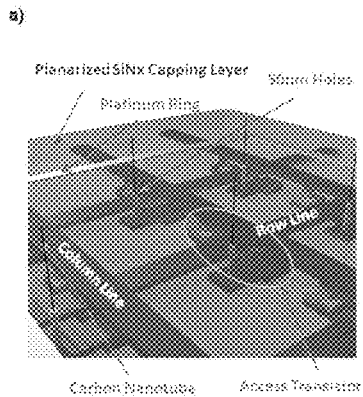
FIG. 1A is a schematic view showing a nano-probe array used to interrogate cells, in accordance with embodiments of the present disclosure.
Figure 1B:
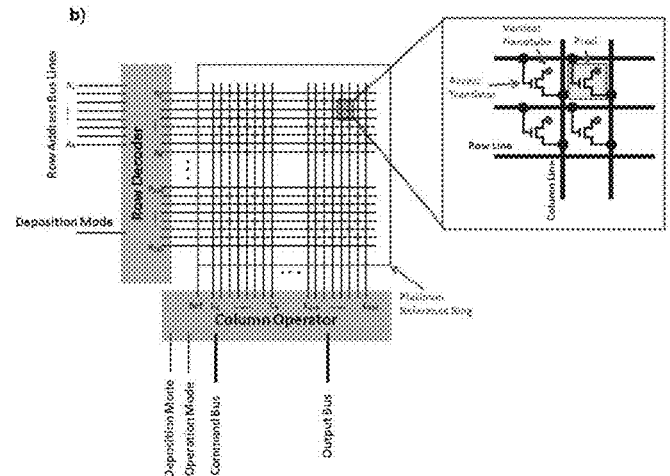
FIG. 1B is a schematic view of a 256 line×256 line bio nano-probe chip.

The nanoscope chip is implemented in a cross-point architecture comparable but different to standard dynamic random access memory (DRAM) technology. A schematic is shown in FIG. 1A-1B. FIG. 1A is a carton showing the nano-probe array used to interrogate cells. FIG. 1B is a Schematic of a 256 lines×256 lines bio nanoprobe chip. The chip consists of three main sections: the row decoder, column operator, and the nano-probe array. Within the array are pixels consisting of an access transistor and a vertical carbon nanotube. The nanotube is connected to the drain of the access transistor through a nanoscale hole in a dielectric capping layer such as aluminum oxide or silicon nitride. The thickness of the capping layer and the diameter of the hole leading to the metal are important parameters and are discussed in the section on electrophoresis deposition of carbon nanotubes.

Each nanoscale pixel includes a vertical carbon nanotube, which is accessed through a transistor, called an access transistor. An image can be resolved down to the nanoscale in real time. In one embodiment, an individual pixel is read by activating the pixel's access transistor via raising the corresponding row line to high. The activated transistor then connects its nanotube to a column line, which is used to probe the environment in the vicinity of the nanotube. By measuring the impedance differences between pixels, an image can be formed. In addition, a platinum ring surrounding the array can be used as a reference electrode during liquid measurements. It will be understood that other reference electrodes could be employed. The type of operation performed by the nanotube is determined by a command set to the column operator, which controls all the column lines. The appropriate Row line is selected through commands sent through the row decoder. The chip can be both controlled and read through a computer. The computer could receive at least one process parameter, such as the height of the row line, process the at least one process parameter, and adjust operation of the system based upon processing of the at least one process parameter.

The role of the column operator is to determine the appropriate function to be applied to the nanotubes and pass the resulting information. In addition, the column operator can assist in facilitating deposition of nanotubes based on the value of the deposition mode line.

Figure 2A:
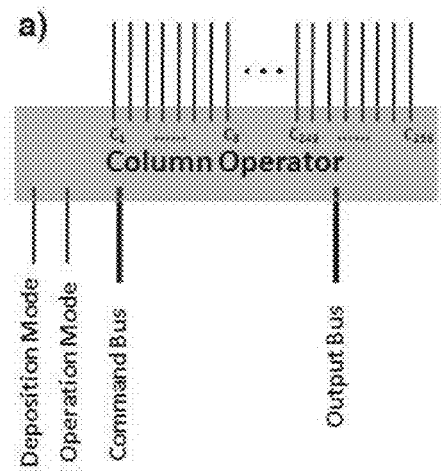
FIG. 2A is a diagram of a column operator.
Figure 2B:
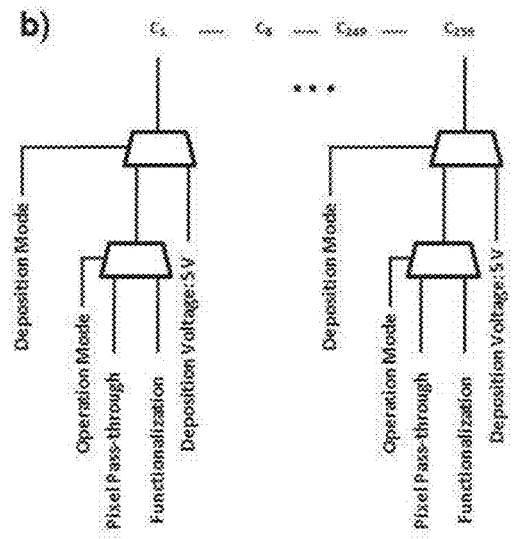
FIG. 2B is a schematic view of multiplexers required to decode the correct operation for each nano-pixel.

As shown in FIG. 2A and FIG. 2B, FIG. 2A is a diagram of the column operator. FIG. 2B is a schematic of the multiplexers connected to the column operator and required to decode the correct operation for each nano-pixel. Both examples are for a 256×256 element device. The logic used to select the correct function is shown in FIG. 2B. Each column line contains two multiplexers, which select the appropriate function based on the Mode lines. The number of multiplexers could vary.

Depending on the embodiment, if the deposition mode line is set to high then all column lines are shorted to a positive voltage (typically 1V to 5V), to allow for electrophoresis deposition of the nanotubes that have a negative charge in suspension. However, if the deposition mode line is off then the column operator looks to the operation mode line to determine the appropriate function for the column lines. When the operation mode line is set to '0', the column lines are passed through the output bus. This action allows the impedance between the nanotubes to be polled by an onboard circuit. In addition, either AC or DC signals consisting of either voltage or current can be applied to interact with the object being imaged. If the operation mode line is set to '1', then the chip enters a functionalization mode. Appropriate columns are connected, based on the command bus to the output bus to enable functionalization of specific targets on specific sites. The output bus is connected to an external circuit used to perform cyclic voltammetry (CV) with can be used as an electrochemical diagnostic and during functionalization of the nanotubes. Simultaneously the platinum ring is also connected to the output bus and is used as a counter electrode during CV. An external reference electrode is used for the CV run. This process is repeated to functionalize different targets.

The row decoder is used to connect a line of nanotubes to their corresponding column lines. An address is sent by the row address bus and is decoded. The row decoder then raises the appropriate row line, thus activating the access transistors connected to that row. The column operator can then perform the programmed function on each nanotube in that row. Once an operation is complete a new address is sent to the row decoder and the process begins again. Once all the rows are scanned an image can be formed on the computer based on the data from the column operator. The chip can scan each row from a frequency of a few hertz up to megahertz, depending on the desired measurement. In addition, the row decoder is also used during electrophoresis. During a deposition, the deposition mode line is activated, signaling the row decoder to short all the row lines to high. This activates all the access transistors, insuring that the drain contacts are connected to their column lines, which are all charged to their intended voltage as required by electrophoresis to deposit the carbon nanotubes. Without activating the deposition mode line, the row decoder functions as previously described.

The chip could be fabricated using standard CMOS processing to fabricate the logic for the column operator, row decoder, access transistors and the row and column lines. The fabrication is performed at the technology node that is required for achieving a specified imaging resolution. The minimum feature linewidth or "critical dimension" determines the minimum spacing between transistors and the associated density of imaging pixels that determines the spatial resolution of the nanoscope.

Figure 3A:
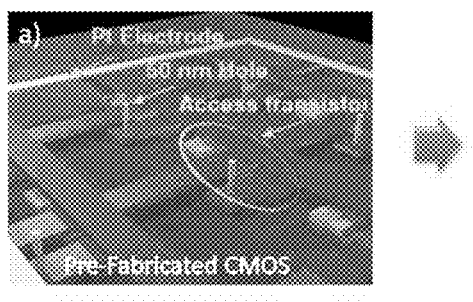
FIG. 3A illustrates initial device fabrication at a foundry using complementary metal oxide semiconductor (CMOS) processing.
Figure 3B:
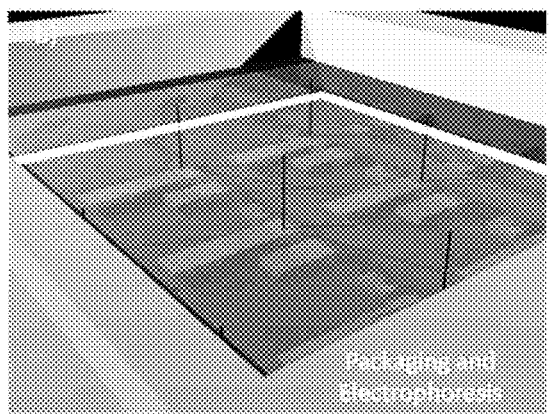
FIG. 3B shows chips that are packaged and subsequent deposition of carbon nanotubes by electrophoresis.

A process diagram is shown in FIGS. 3A and 3B. FIG. 3A illustrates a process flow for chip fabrication, namely CMOS fabricated by a foundry. FIG. 3B illustrates further process flow for chip fabrication, namely chips that are packaged and then carbon nanotubes deposited by electrophoresis. Functionalization can be done afterwards if needed.

Depending on the embodiment, the chip could be capped with a planerized a dielectric capping layer such as aluminum oxide or silicon nitride for both insulation and bio compatibility. 50 nm holes, in one embodiment, could be etched through the dielectric capping layer down to the metal contacts for the drain electrode of the access transistors, using photolithography. The chip could be capped with other suitable layers for insulation and bio compatibility. The chip can then be packaged such that a well is formed around the nano-probe array.

The packaging is another component in the fabrication. It involves making electrical connections from the chip to external circuitry while isolating those connections from the region of the chip that must remain exposed for both further processing and actual use as an imaging device. The intermediary between the external circuitry and the chip could be a chip carrier, which also acts as the consumable product once the chip is attached and finally processed.

There are at least three suggested assembly strategies. One assembly method is to have the contact pads for the chip on the same side of the chip as the active area. In this case the chip could be coated with photoresist first to protect the nanoscale windows from contamination. The resist is not baked to allow for easier removal. The chips are then attached to the chip carrier with adhesive that can cure at room temperature to allow for easier removal of the resist. The resist is removed using the appropriate chemical reagent and electrical contact is made using wires that connect the chip contact pads to the contact pads of the carrier (referred to as wire bonding). The wires and contact pads of both the chip carrier and the chip are then coated with an insulating material while leaving the active region exposed. The insulating material may be deposited in liquid form and cured to harden. Protecting the active region can be achieved by directing the insulating material away from it or by covering the active region with a physical barrier such that the insulating material could only flow around but not over the active region.

The second assembly method to package requires that the contact pads for the chip be configured on the opposite side of the chip than the active region. This can be achieved by adding a "through wafer via" process during CMOS processing of the wafers. As a part of this process solder bumps can be deposited on the contact pads before the wafers are diced into chips. A resist may be deposited on the active side of the wafer for protection of the nanoscale windows and removed before solder reflow. Then another resist could be applied to the active side of the wafer to protect it during dicing of the wafer. The chip could be attached by aligning the solder-bumped contact pads with the mating contact pads on the chip carrier. Then the solder is reflowed to wet the contact pads of the chip carrier. An under fill is then injected between the chip and the carrier to fill the regions in-between the solder. The under fill may serve to also isolate the contacts from liquids used in further processing and during use of the nanoscope. There may also be further isolation as described in the previous assembly method.

The third assembly method is to use the through wafer via process as described for backside contacts and to not mount the chips on carriers. This may require a well structure on the front surface of the chip both as a reservoir for liquid and to strengthen the chip for handling. The access to the chip electronics could then be made using temporary contacts to the backside contact pads such as spring loaded contacts.

After assembly of the chips the carbon nanotubes could be deposited using electrophoresis. Finally, depending on the application, the nanotubes can be functionalized using an electrochemical technique that may be facilitated by the platinum ring as the counter electrode. This process allows for the sensitive CMOS processing to occur without contamination from the electrophoresis process and potential thermal damage to the nanotubes from the CMOS processing.

Figure 4A:
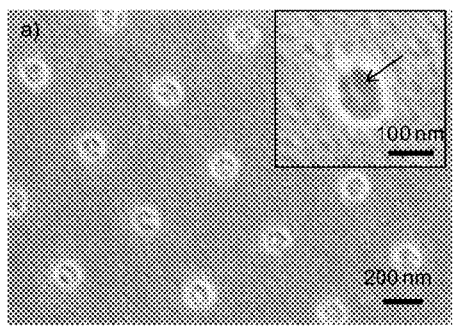
FIGS. 4A-4D show examples of electrophoresis deposition of carbon nanotubes on a metal at the base of nanoscale windows.

A description of electrophoresis deposition (EPD) of vertically oriented carbon nanotubes is generally illustrated in Goyal et al. and related U.S. Pat. Nos. 7,736,979, 8,257,566 and 7,964,143.[1] Examples of EPD of SWCNTs on metal at the base of nanoscale windows are shown in FIGS. 4A-4D. FIGS. 4A-4D illustrate deposition of vertical carbon nanotubes 1 SEM images of electrophoretically deposited SWCNTs. FIG. 4A illustrates high-pressure carbon monoxide (HiPCO) nanotubes sonicated and deposited in approximately 100 nm windows in SiNx on Cr/Co metal on quartz substrate.[7]

Figure 4B:
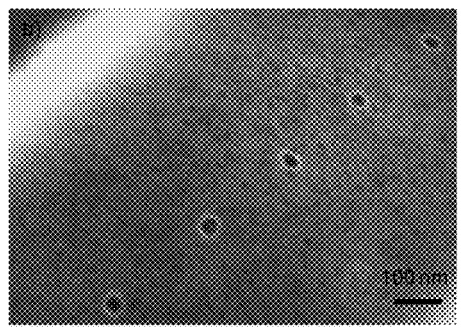
Figure 4C:
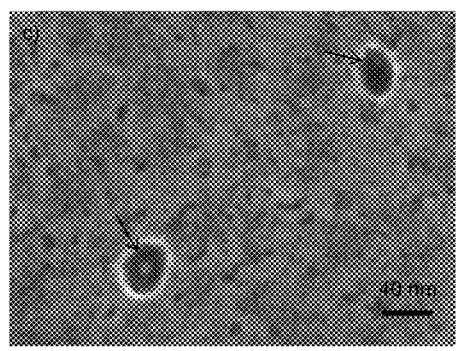
Figure 4D:
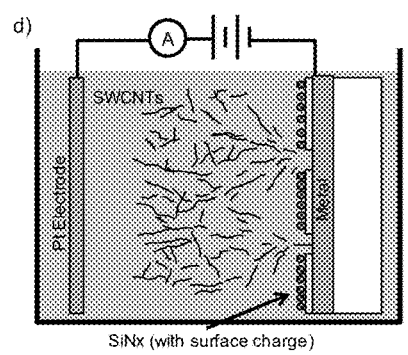

FIGS. 4B-4C illustrate SWCNTs sorted by length[9] to less than 180 nm long deposited in approximately 40 nm windows in SiNx on Cr/Co/Ti metal on Si substrate. The SWCNT deposition was verified with micro-Raman spectroscopy. FIG. 4B is in 100 nm scale, and FIG. 4C is in a magnified 40 nm scale of the same photograph as FIG. 4B. FIG. 4D is a schematic diagram of electrophoresis deposition of SWCNTs.

The EPD process is summarized in FIG. 4D. Pre-synthesized and presorted SWCNTs are suspended in a solution with an appropriate surfactant. The surfactant adds charge to the nanotubes and stabilizes the suspension. The nanotubes are deposited on a metal-coated substrate by electrostatic attraction when a voltage is applied between the substrate metal and another electrode (see FIG. 4D). The adhesion mechanism is an electrochemical interaction between the SWCNTs and the metal contact. Depositing a thin insulating layer over the metalized substrate and opening very small windows to the metal can control the area of deposited nanotubes. Surface charge builds up on the insulator (from mobile ions in the suspension) and creates nanoscopic electrostatic lenses around the windows (see FIG. 1e). The first SWCNT that attaches to the base of the window modifies the electric field and limits the deposition of additional SWCNTs. If the window is small enough the first nanotube always precludes the deposition of others in the same window. The diameter of the hole will be in a range that allows for optimal deposition of single carbon nanotubes or single small bundles whose diameters are smaller than the effective diameter of any functional molecule (such as an enzyme or aptamer) that will be later deposited on the carbon nanotube or bundle. This may thereby limit the number of functional molecules to one per pixel. This limitation to a single enzyme per pixel simplifies the self-diagnostic capability of the device by making it possible to distinguish between cases where the detected signal is from a change in the level of detected chemical versus denaturation or loss of attachment of the enzyme. A similar argument can be made for aptamers. To achieve single nanotube deposition the ratio of the depth of the hole to its diameter should be in the range from 1 to 2 while simultaneously the ratio of the length of the carbon nanotube to the depth of the hole should be in the range from 1 to two. For single wall carbon nanotubes whose average length is 85 nm, a 50 nm window that is 75 nm deep could satisfy this condition in one embodiment. The length of the nanotube is also important and should be on the order of the depth of the window to maximize the number of windows that have deposited nanotubes. Once the nanotubes are deposited the success of deposition at each pixel can be determined by measuring current voltage characteristic using the method described in the Appendix.

The unique properties of the array lend the technology broad versatility for mapping the properties of objects in close proximity of the sensors while in liquids. That includes biological samples such as cells in suspension and tissue. Live cell samples can be imaged. The properties of the cells and their surroundings can be detected using a localized impedance measurement, the electrical potential difference between the cytoplasm and the cell medium, and the local concentration of molecules and ions.

Impedance Mapping—The impedance between two adjacent vertical carbon nanotubes is a function of the dielectric properties of the region near the pair.[5] One imaging mode is to program the access of the deposited carbon nanotubes to measure the impedance between adjacent pairs in a sequence and construct a map of the dielectric properties. It is important to note that an optical microscope achieves this by a completely different method since it creates the map by detecting the reflection or transmission of light directed to the sample. For the device suggested here the dielectric properties can be derived by measuring the capacitance and determining the geometrical factor of the pair of carbon nanotubes. For example if measuring the capacitance, C, of an ideal pair of parallel metal plates the geometrical factor is the area of each plate, A, divided by the distance between the plates, d, and $C = A \varepsilon_r \varepsilon_0 / d$. $\varepsilon_r$ and $\varepsilon_0$ are the relative dielectric permittivity and the permittivity of free space, respectively. To determine the geometrical factor for the carbon nanotube pair one can measure the capacitance of a known material such as distilled/deionized water and calculate the geometrical factor. This can be mapped for the array to account for variations due to length and spacing.

Membrane Potential Mapping—The carbon nanotubes are small enough in diameter to easily pass through the cell wall. They are not to be considered in the same way as traditional rigid (and mostly large) electrical probes in that the force needed to bend the carbon nanotube is vanishing small (even though they are very strong). However, the diameter can be so small (~1 nm) that it is on the order of the thickness of the cell wall (phospholipid membrane). In that case the carbon nanotube can pass through the cell wall in a similar fashion to other molecules and indeed it has been shown that carbon nanotubes in solution with cells end up inside the cells. For the carbon nanotube array one end of each carbon nanotube is connected to an electronic circuit. So there is a possibility to electrically probe the interior of the cell in a similar fashion as a path clamp except that the array may be able to map local variations in the potential difference such as in the neighborhood of ion channels imbedded in the wall of the cell membrane. For membrane potential mapping one can measure the voltage of each probe referenced to either another carbon nanotube or to a platinum electrode incorporated into the device. There is the potential to perform this mapping at relatively high speed and image the dynamics and electrical interplay between different parts of the cell.

Concentration Map of Molecules and Ions—The carbon nanotube platform and particularly the properties of the deposited nanotube allow for the attachment of functional molecules at each pixel. There is also the possibility of attaching different molecules to different sites on the same device.[6, 7] Molecules that have a net electrical charge in suspension can be drawn toward a specific carbon nanotube using an electric field generated between the nanotube and a reference electrode in a similar way as electrophoresis deposition. The advantages are control over the location and the speed of the deposition process, since there is a finite probability that in a suspension of the target molecules there may be unintended deposition on other carbon nanotubes, but this deposition is very slow compared to electric field directed deposition and the electric field preferentially directs the molecules where wanted. The value of having this ability to selectively deposit functional molecules is that these molecules can be used to detect specific targets. Enzymes that catalyze specific molecules or ions are candidates for attachment particularly if they generate one or more electrons during the catalysis that can be detected by the carbon nanotube. These are attractive because the rate of electron generation (i.e., current) is proportional to the concentration of the agent that is catalyzed. The measurement circuit could have an input resistance that could draw power from the enzyme. One could measure the steady state current after initial transients have settled or analyze the transient behavior. The temporal behavior of the initial transient current is also related to the concentration of the target molecule. Measuring the transient response may also allow for more rapid data collection, which is an advantage for high-speed imaging.

Other molecules that could alter the conductivity of the composite (nanotube/molecule) when a target is present may also be candidates for attachment including aptamers. For aptamers the rate of attachment of target is a measure of the targets concentration in the vicinity of where the analysis is done. Since the attachment to the aptamer is inherently permanent (without other interventions) at least two aptamers that are preferably in close proximity are needed to measure the rate. This method requires measuring the impedance or conductance across of each pixel at a rate faster than the attachment rate of the target. One scenario is to inhibit the function of the aptamer using a hairpin oligonucleotide until the measurement is started. A nucleic acid effector is used to "switch the aptamer on". One important application is to use enzymes or aptamers attached to the carbon nanotubes to map the concentration of molecules around or even in biological cells. This could be done dynamically as the cell functions and responds to stimuli.

One unique feature of this platform is that it allows for a single functional molecule to be deposited at the end of the carbon nanotube. As an example a single glucose oxidase enzyme has been deposited at the end of a carbon nanotube and verified by its catalysis of glucose in solution. The evidence for deposition of a single glucose oxidase molecule is that it must attach to a carboxyl group on the carbon nanotube. This group exists on dangling bonds at the tip where the nanotube was cut before sorting (by length). The combination of the geometry of the carbon nanotube and the electric field that it generates during the deposition and the specific requirements for the enzyme to bond makes single enzyme deposition the most probable outcome. The features that become available from this level of control are very important to the operation of the microscope and other applications.

One key feature is that it becomes possible to detect that the enzyme is functioning on each nanotube in a similar way that the nanotube deposition can be detected at each site (see the appendix). As an example, assume that that an array of the carbon nanotubes has a glucose oxidase enzyme attached at each site and is covered with a liquid that has glucose. Each time a glucose molecule is catalyzed by the glucose oxidase enzyme it could generate two electrons that can be transferred to the carbon nanotube and detected by a circuit connected to the carbon nanotube. The rate of electron transfer or current is proportional to the concentration of the glucose. The efficiency of the transfer of electrons from the glucose catalysis to the carbon nanotube could vary depending on the exact attachment site of the enzyme.

The further away from the catalysis site that the glucose oxidase is from the carbon nanotube the lower the current. Therefore, a sample of the currents from several glucose oxidase/nanotube sensors could have a distribution that represents the range of possibilities at a specific concentration of glucose. It should be possible to generate a calibration curve of current versus glucose concentration for each sensor and for an ensemble of sensors. Assuming that all working sensors will trend the same way for the same glucose concentration, one can identify outlier behavior as a failure of a sensor within the ensemble.

One of the failure modes could be denaturing of the enzyme. In this case there could be no current from the catalysis of glucose. It is then possible to modify the calibration table for the ensemble by eliminating the inactive sensor contribution. That is, a current drop in the ensemble would not necessarily be attributed to a drop in glucose concentration, but non-working sensors in the ensemble. This is possible as long as the operation of single sensors can be measured separate from others, which is an essential attribute of the microscope operation. Once the non-functional pixels are identified the calibration table could be updated for the ensemble. This degree of self-recalibration is made possible by having a single enzyme at the tip of each carbon nanotube. This could obviously be done with an ensemble of any enzyme that can transfer electrons to the carbon nanotube after catalysis of a target molecule. Finally the self-recalibration feature was described here for a general sensor that is not necessarily an imaging mode. However, it also can be used to detect a non-functioning analytical pixel in the nanoscope.

The unique properties of carbon nanotubes can be used to fabricate an imaging device by first depositing them in a vertical geometry in a circuit such that each one can be accessed individually. The resolution could be determined by the spacing between the carbon nanotubes and can be as small as the size of the access transistor that is used for collecting the signal that could be mapped into an image. There is no optics because the sample interacts with the carbon nanotube either directly or as a byproduct of the action of a functional molecule deposited on the carbon nanotube. This could be a useful tool for cell biology applications among others.

APPENDIX

Contact Analysis of Vertical Carbon Nanotube Devices Deposited Using Electrophoresis With the advent of electrophoretic deposition using electrostatic nanoscopic lenses vertically oriented single wall carbon nanotubes (SWNT) can be deposited at room temperature, making them viable for integration with traditional silicon wafer processing for integrated circuits. However, there is currently a lack of data on the SWNT/metal contact interface using this deposition protocol. By performing current vs voltage (IV) measurements against a platinum wire in a phosphate buffer and by modeling the data, detected is the presence of the nanotube, study the contact interface, and infer the nanotube's viability for device applications. A Schottky barrier height of 0.15 eV±0.02 eV was extracted from the IV curves for a (6,5) SWNT end contact interface with Ti. This value is comparable but slightly less than the predicted value (0.18 eV) for a Ti side contact to the same diameter SWNT as interpolated from reported parametric data. The end contacts of electrophoresis deposited SWNTs to Ti at the base of nanoscale windows have suitable electrical characteristics for many device applications.

Transistor devices based on individual carbon nanotubes have been successfully demonstrated in the lab but have proven difficult to commercialize in part because of variability between transistors.[8, 9] Integration with standard silicon integrated circuit process technologies is difficult.[9, 10] Devices based on carbon nanotubes could significantly improve medical diagnostics and portable energy.[5, 6, 11-13] In these applications and many biosensors a much larger variability in devices is acceptable. Despite this there is still the problem of CMOS compatibility, which may limit the functionality advantages of integrated logic for some devices. The issue is high temperatures that are required to grow the nanotubes are incompatible with CMOS technologies.[14, 15] It was discovered that a possible solution is to use a room temperature deposition method for the carbon nanotubes. This allows devices to be fabricated using standard CMOS processing and the nanotubes to be deposited even after silicon based transistors have been processed. Recently a method has been demonstrated to deposit individual vertical carbon nanotubes in precise locations using electrophoresis and electrostatic nanoscopic lenses.[1] Single wall carbon nanotube (SWNT) based devices have also been made using CMOS compatible processing and electrophoresis to detect various biological cells and generate electrical power from sugar and oxygen[5, 6]

One of the challenges of this platform technology is the characterization of the deposited SWNT. The size of the SWNT (~1 nm diameter) combined with the vertical geometry and the narrow window in which they are deposited (30-50 nm) makes non-destructive electron microscopy difficult. Indeed, just verifying that a SWNT is deposited is a challenge. The metal to SWNT interface is also important since it impacts the operation of devices. There has been significant research into the metal to nanotube interface and the role it plays in performance for more conventional planar devices. These devices have their nanotubes lying flat on a substrate and the metal contact connected to the sidewalls of the nanotubes.[16-19] This information is important to better design devices and to help determine the quality of the fabricated devices during manufacturing. However, there has not been any significant research into the unique contact geometry that results from electrophoresis deposited nanotubes with the use of electrostatic nanoscopic lenses. Vertical geometries have been developed for large area field emission displays, but the physics of the contact interface has not been studied.[20-22] Studies of the contacts have been done for carbon nanotubes grown in place vertically,[15, 23] but not for deposited nanotubes. Electrical characterization of the contacts is difficult in applications where only one end of the SWNT is connected (such as nanoprobe sensors and fuel cells). Metal contacts could be deposited onto the free ends of the SWNTs but this could require post processing after SWNT deposition and could be most useful if the final device requires metal contacts on both ends (i.e., interconnects and transistors).'

Here, in one embodiment, a method is presented that can non-destructively characterize the deposited nanotubes. The method, which is based on making current vs. voltage (IV) measurements, can rapidly determine the presence of the nanotubes. In addition, this technique has the advantage of probing the contact interface between the nanotube and the metal interconnect. This information could help in understanding the physics of the unique contact geometry and could provide a measure of the health of the device.

Figure 5:
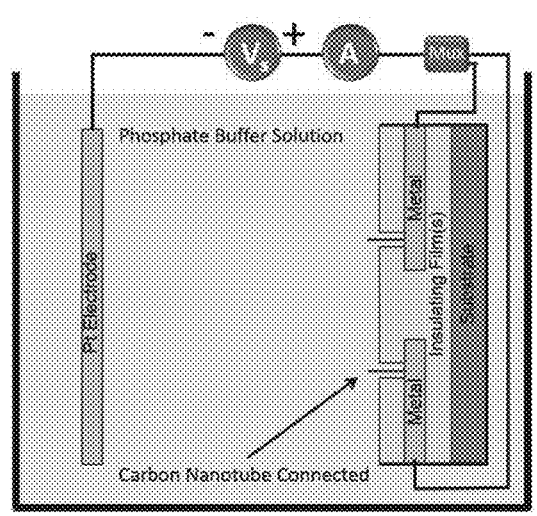
FIG. 5 is a diagram of an experimental setup that includes a carbon nanotube.

Shown in FIG. 5 is an illustrated example of a device fabricated on silicon wafers with 1 micron of deposited silicon-oxide. Further, FIG. 5 illustrates a diagram of an experimental setup to both study and determine electrically the health of the fabricated devices with vertical nanotubes deposited via electrophoresis. A carbon nanotube is selectively connected through a multiplexer (Mux). Depending on the implementation, (14) titanium metal leads may be deposited using e-beam evaporation and photolithography. The Ti leads are one micron wide and fan out to contact pads. Next, 75 nm of silicon nitride was deposited conformably using plasma enhanced chemical vapor deposition (PECVD). 30-40 nm windows, located near the tips of each of the one-micron leads, were defined and opened down to the metal using e-beam lithography and reactive ion etching. Chips are then diced and mounted into dual inline packages. Wire bonding was used to connect the contact pads to the package. The wires and contact pads were sealed using silicone.

Carbon nanotubes were presorted by length.[24] The diameters were determined via optical methods. Based on the observed 40% chirality of (6, 5) the average distribution is about 0.84 nm. To get the true external diameter, the thickness of the excluded volume is added from the thickness of a sheet of graphene (0.34 nm). Thus the true external diameter is about 1.2 nm.[25] The lengths were measured in an SEM to be 83±26 nm.

The carbon nanotubes are deposited using electrophoresis as described in Goyal et. al.[1] A voltage is applied between a platinum wire and the device, which are both submerged in an aqueous suspension of carbon nanotubes. The resulting field pulls in nanotubes into the 30-40 nm windows. The size of the windows restricts the deposition to a single nanotube. Any stray nanotubes are washed away.

IV measurements were performed using an HP 4140b picoammeter. As shown in FIG. 5, chips were placed in a bath of phosphate buffer with one electrode as a platinum wire and the other as the device. Measurements were performed on devices with deposited carbon nanotubes and on devices without nanotubes. It was not possible to deposit carbon nanotubes on samples after IV measurements were recorded.

Figure 6A:
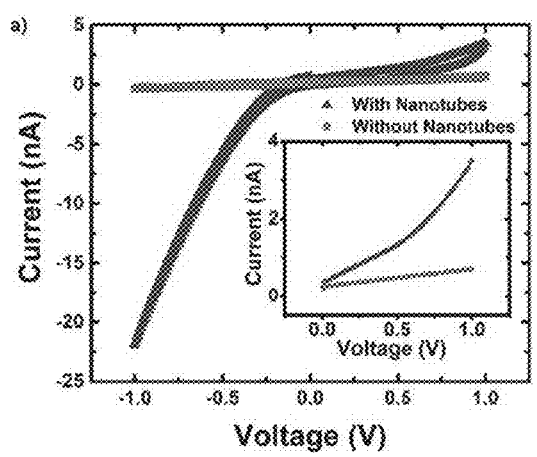
FIG. 6A shows a chart of the average current versus voltage curve of devices with and without naontubes.
Figure 6B:
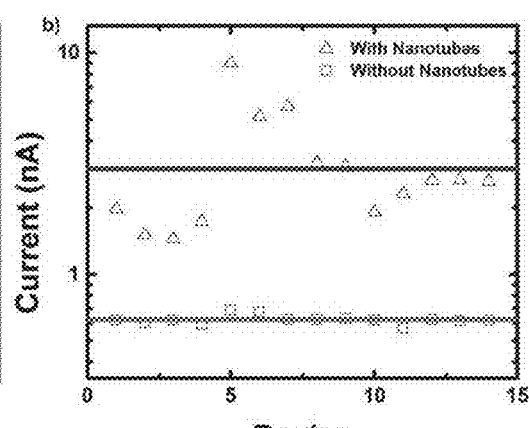
FIG. 6B shows a range of currents for fourteen devices, with and without nanotubes.

FIGS. 6A-6B show the results of IV measurements recorded on samples after carbon nanotube deposition compared to samples before deposition. FIG. 6A illustrates the average current versus voltage curve of devices with and without nanotubes. The scan goes from 0V to 1V then down to −1V and finally back to 0 V. Insert shows the positive range of the voltage from 0 to 1V. FIG. 6B illustrates the range of currents for 14 devices, with and without nanotubes. During the IV sweep, the voltage starts at 0V and is varied up to 1V. Next the voltage is scanned down to −1V, and finally brought back up to 0V. The fact that one electrode is a carbon nanotube connected to a Ti lead and the counter electrode is a macroscopic Pt wire accounts for the asymmetry in the IV curve for these devices. The difference in electrode geometries leads to differences in reaction at the electrode liquid (phosphate buffer) interface. If the voltage is positive, electrons enter the Pt and are used for electrochemical reactions with positive ions at the Pt buffer interface. Negative ions move to the carbon nanotube and through electrochemical reactions, electrons are transferred to the nanotube and are travel into the Ti, through the Ti/carbon nanotube interface. A Schottky barrier for holes is present between the Ti metal and the carbon nanotube. The nanoscale window geometry combined with the geometry of carbon nanotube confines the electrochemical reactions to the exposed tip of the carbon nanotube where the induced electric field is the largest. When the voltage is negative, electrons travel toward the nanotube though the Ti and are used for electrochemical reactions with the phosphate buffer. Unlike in the positive voltage, the higher current in the IV curve suggests that there is no significant barrier for electron or hole conduction in either electrode.

Measurements on samples without nanotubes resulted in a lack of asymmetry in the IV curves. In addition, the IV curves were in the range of hundreds of picoamps as opposed to nanoamps for devices with nanotubes. The lack of asymmetry and lower current when no nanotubes were deposited suggest the role that the nanotubes play. One possible explanation is that the nanotube allows for easier access to the buffer. Without a nanotube, the buffer has to penetrate a 30-40 nm window that is 75 nm deep, which is exceptionally difficult given the small geometry, the aspect ratio, and the surface tension of water. When a nanotube is connected to a device, it extends beyond the hole and into the liquid, allowing for intimate contact between the buffer and the nanotube. Considering the unique size and aspect ratio of the windows and the length of the nanotubes (mean length ~83 nm), it can be inferred that nanotubes are relatively vertical. With a window diameter of 30-40 nm and a depth of 75 nm, the maximum angle from completely vertical is 21 to 28 degrees. This could allow for the nanotube to just reach the surface of the chip. The one to two order magnitude difference in the current between devices with and without nanotubes could be also attributed to the differences in aspect ratio. The sharper tips of the 1.2 nm diameter nanotubes compared to the 30-40 nm diameter windows enhance the electric field. The asymmetry in the IV curve can be an indication of the presence of a nanotube within the device.

The effects of the surfactant used during deposition of the SWNTs also need to be considered. A stable suspension is critical to the electrophoresis deposition process. This involves mixing a surfactant with the SWNTs in an aqueous solution. The surfactants wrap around the SWNTs.[24] After deposition the surfactant rinses clean from the substrate, but it is difficult to detect the extent that it rinses from the SWNT. The surfactant may act as an effective passivation of the sides of the SWNTs and further concentrate the charge conduction to the tip.

Further evidence is provided by looking at the distribution of current ranges across the 14 devices. For the case with nanotubes, the variation in the range of currents is much larger than that of devices without nanotubes, as shown in FIG. 6b. Devices without nanotubes showed a very narrow distribution, staying in the range of $10^{-10}$ A. While devices with nanotubes show a much larger distribution ranging from $10^{-9}$ to $10^{-8}$ A. The large variation suggests the conduction in the circuit is strongly coupled to the presence of the carbon nanotube. The distribution is also an indication of variation in the devices. This variation could be due to some devices having single nanotubes while others could have small bundles. This could change the contact area giving the variation of current range. Another possible reason for the large variation in current could be in the contact interface between the nanotube and titanium.

Figure 7A:
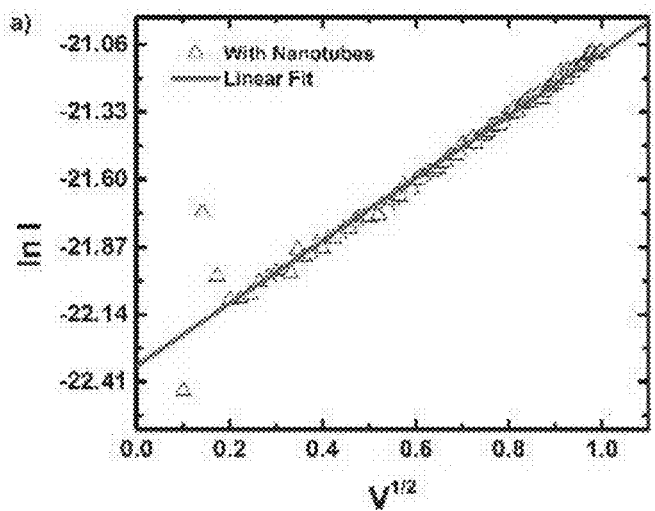
FIG. 7A is a fit to a Schottky barrier model for an average IV curve, from 0 to 1V.

To look at the contact interface, the IV curves from 0-1V (FIG. 6a insert) were fitted with a Schottky barrier (SB) model. The equation used is:

$$J = AA^*T^2\exp\left(-\frac{\phi_b}{kT}\right)\exp\left[\frac{e}{kT}\left(\frac{eV}{4\pi\varepsilon_0\varepsilon_r}\right)^{1/2}\right] \quad (0.0)$$

Where A is the contact area, A* is the Richardson constant, T is temperature in kelvin, $\Phi_b$ is the barrier height, k is Boltzmann constant, e is the fundamental charge, V is the applied voltage, $\varepsilon_0$ is the dielectric constant, and $\varepsilon_r$ is the dielectric constant of a nanotube. The resulting fit of the average current is shown in FIG. 7A. FIG. 7A illustrates a fit for a Schottky barrier (SB) model for the average IV curve, from 0 to 1V.

Figure 7B:
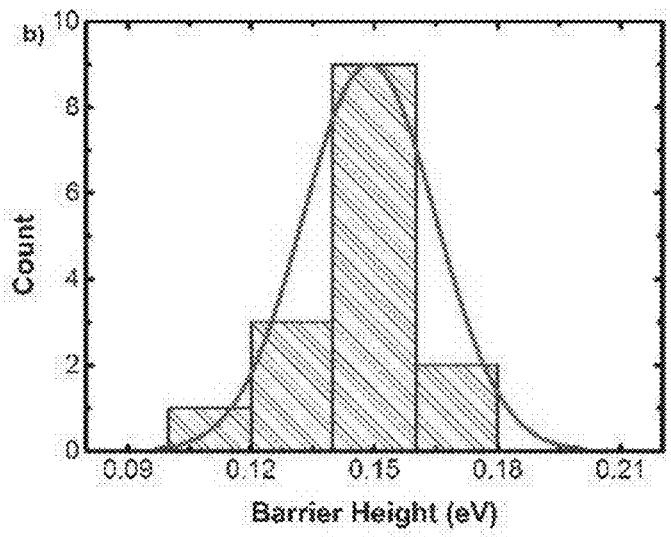
FIG. 7B is a histogram of calculated barrier heights for the fourteen devices that were measured; and, FIG. 7C is a histogram of the range of current for the fourteen devices.
Figure 7C:
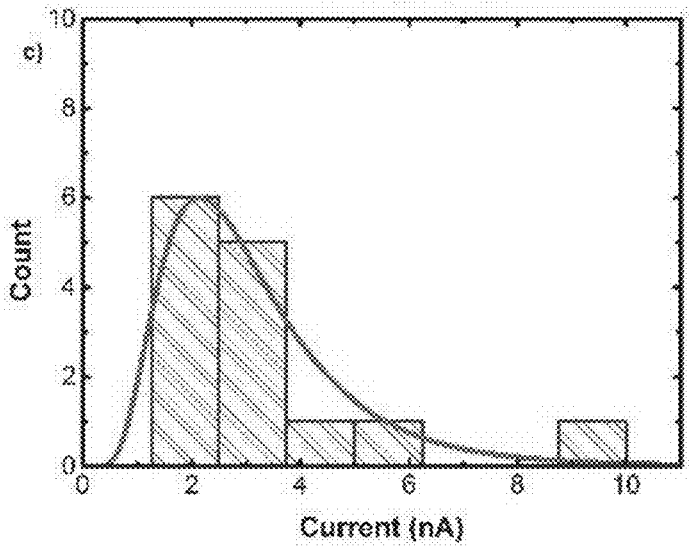

Using a diameter of 1.2 nm, the Schottky barrier height for the average IV (0-1V) curve is 0.15 eV±0.02 eV. 0-1V was chosen since the system was unmodified by a previous voltage. After 1V a hysteresis was observed indicating that the interface between the contact and the buffer was changed, either by charge storage through a double layer or other electrochemical reaction. The calculated barrier heights derived the measurements reported here agree with SWNT devices with titanium contacts.[25] FIG. 7B shows the distribution of extracted barrier heights for the various IV curves. Further, FIG. 7B illustrates a histogram of calculated barrier heights for the 14 devices that were measured. The distribution is narrow with a barrier height of 0.15 eV as the highest probability of being measured. The distribution of barrier heights is not consistent with the distribution of current ranges (FIG. 7C). FIG. 7C further illustrates a histogram of the range of current for the 14 devices that were measured. Unlike for barrier heights, the distribution is logarithmic with a bias towards the low nano-amp range. The very different histograms suggest that the variation in current ranges is not due to the contact interface. In fact the narrow distribution of barrier heights and the agreement with the literature suggests that the nanotubes are depositing cleanly and making good electrical contact to the titanium metal. The variation in device performance appears to be due to another factor.

Looking closely at the distribution of current in FIG. 7C, the highest probability of current is 2.14 nA. The probability of having a device with a measured current below that is very small, in fact no device had a current below 1.45 nA. However there is a larger chance of currents above 2.14 nA. The presence of larger currents and the barrier height analysis suggest that the electrical interactive regions of the nanotube are clean. If there were contaminates in these locations, probabilities of measuring lower currents than 2.14 nA could be much higher. One explanation of the preference for higher currents could be the presence of small bundles (2-3 nanotubes). A similar analyses was done for nanotubes that were grown in place by Franklin et. al.[1]. There is a finite probability of having small bundles in a stable solution. As such, there is a small probability that the nanotube that could be deposited into the hole could be a small bundle, as opposed to a single nanotube. Comparing the highest measured current (9.37 nA) to the highest probability current (2.14 nA), a ratio of 4.37 is obtained. This could correspond to an increase in diameter of the contact area from 1.2 nm to 2.4 nm. And if looking at the 2nd highest current (which falls within the distribution curve) a ratio of 2.6 is obtained, corresponding to an increase in diameter to 1.94 nm. The increase in diameter is reasonable for a small bundle. Another possible reason for an increase in contact area could be a sidewall contact (versus end contact) between the nanotube and the Ti metal. The length fractionation procedure used to sort the SWNTs leaves them straight within this range of lengths.[26] Since the nanotubes were straight before deposition, the geometry of the window and the dynamics of the SWNT under the influence of the electric field forces the end to make first contact with the metal at the base. It is straightforward to show that there is not enough energy (by many orders of magnitude) during the approach of the SWNT to buckle it on impact with the metal. Transmission electron microscopy (TEM) would be required to better understand the physical contact that the nanotube is making. It could also help to verify the presence of small bundles in some of the devices.

In summary, it was detected that a Schottky barrier forms between SWNTs and TI when deposited using electrophoresis and electrostatic nanoscopic lenses. Barrier heights were extracted by modeling the IV data of various carbon nanotube devices against a platinum wire immersed in a phosphate buffer. A narrow distribution of barrier heights with a median of 0.15 eV was found. This is in agreement with other carbon nanotube devices with titanium contacts. This suggests that the deposition of vertically oriented nanotubes onto the titanium metal is very clean, despite the surfactants within the nanotube suspension. Surfactants deposited between the nanotube and titanium may cause a much larger spread of barrier heights and a deviation from 0.15 eV. Understanding the barrier height can lead to better and unique devices that require precise control of the contact interfaces. This information can also be used to determine the quality of the contacts in multiple devices for manufacturing. In addition the distribution of current ranges could indicate the number of nanotubes that could be present. However more experiments will be required to correlate the current range with the number of nanotubes. A method can be developed to rapidly determine the health of multiple devices by measuring IV characteristics in a buffer and multiplexing through a test fixture across a wafer. This diagnostic tool could help to enable mass production of vertical nanotube based electrical devices.

Figure 8:
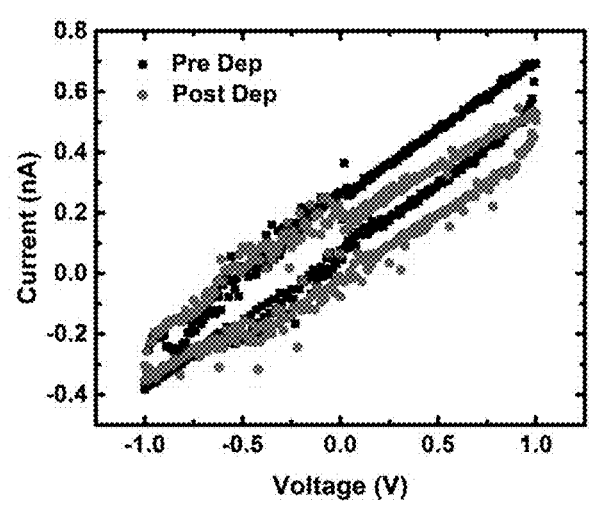
FIG. 8 Comparison of IV before and after attempts to electrophoresis deposit carbon nanotubes on Ti at the base of nanoscale windows.

Contact Analysis of Vertical Carbon Nanotube Devices Deposited Using Electrophoresis I. Modification of Nanoscale Windows During IV Measurements in Buffer Solution It was not possible to use electrophoresis to deposit carbon nanotubes on the metal at the base of the nanoscale windows after an IV was recorded in buffer solution. A comparison of IV measurements before and after deposition of nanotubes is shown in FIG. 8. More particularly, FIG. 8 illustrates a comparison of IV before and after attempts to electrophoresis deposit carbon nanotubes on Ti at the base of nanoscale windows. There is a slight change in slope indicating that the resistance increases after an attempt to deposit nanotubes, but the two are otherwise very similar. There is no indication in the IV of a Schottky barrier. Whereas, comparison of pre-deposition IV measurements with post-deposition samples that were not measured before the deposition are dramatically different (see FIG. 2A). A detailed explanation of the interaction of the phosphate buffer with the windows during an IV measurement (without deposited nanotubes) is complicated because of the size of the window. That is, the combination of the hydrophobicity of the SiNx and the aspect ratio of the nanoscale windows have to be taken into account when modeling whether and how the liquid will interact with the Ti. A detailed analysis is beyond the scope of this paper. However, it should be pointed out that changing the shape of the window by electrodeposition of material on the SiNx around the window could effectively limit the electrophoresis deposition of nanotubes without modifying the properties of the Ti. Also, the IV measurement after nanotube deposition does not appear to degrade the ability to functionalize the tip of the nanotube with an enzyme. Measured are catalysis of glucose by glucose oxidase using IV characterized nanotubes.

II. Analysis of Carbon Nanotube Impact During Electrophoresis Deposition

The kinetic energy of the carbon nanotube during electrophoresis deposition is straightforward to calculate. The carbon nanotube in an aqueous suspension under the influence of an electric field, E, reaches a drift velocity, v, that is determined from this expression[27]

$$v = \mu E = \frac{\varepsilon_{rs}\varepsilon_0 \zeta}{\eta} E \quad (S1)$$

where $\mu$, is the mobility, $\varepsilon_{rs}$ is the relative permittivity of the electrolyte medium, $\varepsilon_0$ is the permittivity of free space and $\eta$ is the viscosity. The zeta potential $\zeta$, is defined as the potential at a distance from the surface of the particle where fluid is free to flow around the particle (referred to as the slip plane). $\zeta$ of the nanotube suspension that was used in this research was measured. Only the maximum $\zeta$ is important for the purpose of this analysis, which was ~−103 mV. The maximum E used during deposition was 1 V/cm. However, as much as 10 V/cm have been used in other experiments. Using $\varepsilon_{rs}$=80 and $\eta$=8.9×10$^{-4}$ Pa-s (for water), the maximum velocity, $v_{max}$ is 8.2×10$^{-6}$ m/s. To calculate the mass it is assumed (6,5) chirality single wall carbon nanotubes that are 83 nm long. This leads to a mass, $m_{SWNT}$ of 1.48×10$^{-22}$ kg and a kinetic energy, K.E., of 5×10$^{-33}$ J. This needs to be compared to the energy required to bend the SWNT.

After the SWNT makes its initial contact with the metal at the base of the window, there are two possible scenarios. The first is that the SWNT bonds with the metal and any energy left in the nanotube will start it to bend analogous to a beam becoming compressed under its own weight. The other possibility is that the SWNT approaches the metal at an angle and the end slides along the metal until it reaches the side of the window. It may also start to bend at this point with one end now fixed. One might consider using buckling theory for the carbon nanotube under either of these scenarios, but the length of the nanotubes used in these studies is so long compared to the diameter that it can support significant bending under compressive stress.[28] It useful then to consider a simple bending scenario for the SWNT and see if the energy required is within a range that would warrant a more rigorous calculation. Chosen was a cantilever arrangement for this purpose where the end is fixed and the free end is deflected by a small distance corresponding to an angle of ~1 deg. In reality the SWNT would have to bend nearly 90 deg to make a side contact with the metal at the base of a window. However, the small angle approximation will be instructive. The energy stored in the deflected cantilever consisting of a rod that has an effective spring constant k given by[29]

$$k = \frac{3E_Y I}{L^3} \quad (S2)$$

where $E_Y$ is the Young's modulus (~1.2 TPa), L is the length and the area moment, I, is given by $$I = \frac{\pi(D_0^4 - D_i^4)}{64}. \quad (S3)$$

Here $D_0$ and $D_i$ are the outer and inner diameters, respectively, of the SWNT. Depending on the implementation 1.2 nm and 0.4 nm may be used for these, but this does not take into account that there is likely a layer of surfactant wrapped around the SWNT, which will increase I. The potential energy, V, that is stored in the bent SWNT is then $$V = \frac{1}{2}kx^2 = \frac{3E_Y \pi (D_0^4 - D_i^4)}{128 L} \sin^2\theta \approx 6.7 \cdot 10^{-22} \text{ J} \quad (S4)$$

There is clearly not enough kinetic energy (~5×10$^{-33}$ J) in the drifting SWNT to bend it onto the metal surface on impact. Therefore, an end contact of the SWNT with the metal at the base of the window is highly probable.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

REFERENCES

[1] A. Goyal, S. Liu, Z. Iqbal, L. A. Fetter and R. C. Farrow, Journal of Vacuum Science and Technology B 26, 2524-2528 (2008).
[2] R. C. Farrow and A. Goyal, U.S. Pat. No. 7,736,979 (2010).
[3] R. C. Farrow, Z. Iqbal, A. Goyal and S. Liu, U.S. Pat. No. 8,257,566 (2012).
[4] R. C. Farrow, A. Goyal, Z. Iqbal and S. Liu, U.S. Pat. No. 7,964,143 (2011).
[5] A. Kanwal, S. Lakshmanan, A. Bendiganavale, C. T. Bot, A. Patlolla, R. Raj, C. Prodan, Z. Iqbal, G. A. Thomas and R. C. Farrow, Biosensors and Bioelectronics 45 (0), 267-273 (2013).
[6] A. Kanwal, S. C. Wang, Y. Ying, R. Cohen, S. Lakshmanan, A. Patlolla, Z. Iqbal, G. A. Thomas and R. C. Farrow, Electrochemistry Communications 39 (0), 37-40 (2014).
[7] R. C. Farrow, Z. Iqbal and A. Kanwal, U.S. Pat. No. 8,546,027 (2013).
[8] S. Park, M. Vosguerichian and Z. Bao, Nanoscale 5 (5), 1727-1752 (2013).
[9] M. F. L. D. Volder, S. H. Tawfick, R. H. Baughman and A. J. Hart, Science 339 (6119), 535-539 (2013).
[10] D.-M. Sun, C. Liu, W.-C. Ren and H.-M. Cheng, Small 9 (8), 1188-1205 (2013).
[11] H. T. Jeong, B. C. Kim, M. J. Higgins and G. G. Wallace, Electrochimica Acta 163 (0), 149-160 (2015).

[12] I. Yoon, K. Hamaguchi, I. V. Borzenets, G. Finkelstein, R. Mooney and B. R. Donald, PLoS ONE 8 (6), e65715 (2013).

[13] J. Lu, S. Liu, S. Ge, M. Yan, J. Yu and X. Hu, Biosensors and Bioelectronics 33 (1), 29-35 (2012).

[14] J.-P. Tessonnier and D. S. Su, ChemSusChem 4 (7), 824-847 (2011).

[15] A. P. Graham, G. S. Duesberg, W. Hoenlein, F. Kreupl, M. Liebau, R. Martin, B. Rajasekharan, W. Pamler, R. Seidel, W. Steinhoegl and E. Unger, Applied Physics A: Materials Science & Processing 80 (6), 1141-1151 (2005).

[16] P. Bal, E. Li, K. T. Lam, O. Kurniawan and W. S. Koh, Nanotechnology 19 (11), 115203 (2008).

[17] S. Krompiewski, Nanotechnology 18 (48), 485708 (2007).

[18] A. D. Franklin, D. B. Farmer and W. Haensch, ACS Nano (2014).

[19] Z. Chen, J. Appenzeller, J. Knoch, Y.-m. Lin and P. Avouris, Nano Letters 5 (7), 1497-1502 (2005).

[20] W. B. Choi, Y. W. Jin, H. Y. Kim, S. J. Lee, M. J. Yun, J. H. Kang, Y. S. Choi, N. S. Park, N. S. Lee and J. M. Kim, Applied Physics Letters 78 (11), 1547-1549 (2001). [21] C.-C. Xiomara, G. Huaizhi, G. Bo, A. Lei, C. Guohua and Z. Otto, Nanotechnology 20 (32), 325707 (2009).

[22] G. Bo, G. Yue, Q. Yue, Y. Cheng, H. Shimoda, L. Fleming and O. Zhou, Advanced materials 13 (23), 1770-1773 (2001).

[23] A. D. Franklin, R. A. Sayer, T. D. Sands, D. B. Janes and T. S. Fisher, Nanotechnology, IEEE Transactions on 8 (4), 469-476 (2009).

[24] J. A. Fagan, M. L. Becker, J. Chun and E. K. Hobbie, Advanced Materials 20 (9), 1609-1613 (2008).

[25] J. Fagan, (2012).

[26] M. S. Arnold, J. Suntivich, S. I. Stupp and M. C. Hersam, ACS Nano 2 (11), 2291-2300 (2008).

[27] A. V. Delgado, F. Gonzalez-Caballero, R. J. Hunter, L. K. Koopal and J. Lyklema, in Pure and Applied Chemistry (2005), Vol. 77, pp. 1753.

[28] B. I. Yakobson, C. J. Brabec and J. Bernholc, Physical Review Letters 76 (14), 2511-2514 (1996).

[29] J. M. Kinaret, T. Nord and S. Viefers, Applied Physics Letters 82 (8), 1287-1289 (2003).

What is claimed is:

1. An analytical nanoscope for sub-optical resolution imaging, comprising, a complementary metal oxide semiconductor (CMOS) chip or charge-couple device (CCD) image sensor; a plurality of nano-pixels forming an array of vertically oriented carbon nanotubes sensors or a nano-probe array, the carbon nanotubes disposed on the CMOS or the CCD;
wherein, the carbon nanotubes are functionalized to provide chemical information about a sample, and the nanoscope functions in a lightless environment collecting information directly from the sample by making contact or converting information from a functional molecule of the sample; and
wherein the CMOS further comprises a row decoder, and a column operator, the nano-probe array, and a packaging, wherein the packaging includes a plurality of electrical connections from the chip to an external circuitry, and the electrical connections are isolated from a region of the chip that remains exposed.

2. The analytical nanoscope of claim 1, wherein the CMOS further comprises a row decoder, and a column operator, and the nano-probe array, and wherein the row decoder is used to connect a line of nanotubes to corresponding column lines.

3. The analytical nanoscope of claim 2, wherein within the array are a plurality of pixels consisting of an access transistor and a vertical carbon nanotube.

4. The analytical nanotube of claim 3, wherein the vertical carbon nanotube has a connection to a drain of the access transistor.

5. The analytical nanotube of claim 4, wherein the connection is through a silicon nitride capping layer defining a hole approximately 50 nm in diameter.

6. The analytical nanoscope of claim 1, further including a chip carrier for acting as an intermediary between the external circuitry and the chip.

7. The analytical nanoscope of claim 1, wherein the column operator determines an appropriate function applied to the nanotubes and passes resulting information.

8. The analytical nanoscope of claim 7, further including a plurality of multiplexors connected to the column operator, and wherein the multiplexors decode correct operation for each nano-pixel.

9. A process used in an analytical nanoscope for sub-optical resolution imaging comprising,
resolving an image down to a nanoscale in real time;
wherein the analytical nanoscope includes a plurality of nano-pixel, and each nano-pixel includes a vertical carbon nanotube forming an array disposed on a semiconductor chip, and each vertical carbon nanotube is accessed through an access transistor;
reading an individual pixel by activating the pixel's access transistor via raising a corresponding row line to high; and then having the activated transistor connect its nanotube to a column line used to probe an environment in a vicinity of the nanotube;
measuring impedance differences between pixels to form an image; and
using as a reference electrode a platinum ring surrounding the array during liquid measurements.

10. The process of claim 9 further includes reading and controlling the chip through a computer, wherein the computer receives at least one process parameter, processing the at least one process parameter, and adjusting operation of the system based upon processing of the at least one process parameter.

11. Method of making an analytical nanoscope for sub-optical resolution imaging comprising,
positioning contact pads for a semiconductor chip on a same side of the chip as an active area, or positioning contact pads for the chip on the opposite side of the chip than the active region, or using a through wafer via process for backside contacts;
coating the chip with photoresist to protect a nanoscale window from contamination;
attaching the chip to a chip carrier with an adhesive if not using a through wafer via process;
removing the resist with a chemical reagent and making electrical contact using wires that connect the chip contact pads to the contact pads of the carrier;
coating the wires and contact pads of both the chip carrier and the chip with an insulating material while leaving an active region exposed;
after assembly of the chips using an electrophoresis process to deposit the carbon nanotubes; and
functionalizing the nanotubes using an electrochemical technique facilitated by a platinum ring as a counter electrode to allow for complementary metal oxide semiconductor (CMOS) processing to occur without contamination from the electrophoresis process and potential thermal damage to the nanotubes from the CMOS processing.

* * * * *